US00PP31341P2

(12) United States Plant Patent
Hoogkamp

(10) Patent No.: US PP31,341 P2
(45) Date of Patent: Jan. 7, 2020

(54) ***CURCUMA* PLANT NAMED 'CURDOSSIMP'**

(50) Latin Name: *Curcuma alismatifolia*
Varietal Denomination: Curdossimp

(71) Applicant: Timothy Johan Herman Hoogkamp, Doetinchem (NL)

(72) Inventor: Timothy Johan Herman Hoogkamp, Doetinchem (NL)

(73) Assignee: Nubilus B.V., Naaldwijk (NL)

( * ) Notice: Subject to any disclaimer, the term of this patent is extended or adjusted under 35 U.S.C. 154(b) by 0 days.

(21) Appl. No.: 16/350,882

(22) Filed: Jan. 28, 2019

(51) Int. Cl.
*A01H 5/02* (2018.01)

(52) U.S. Cl.
USPC ..... Plt./421
CPC ..... *A01H 5/02* (2013.01)

(58) Field of Classification Search
USPC ..... Plt./421
CPC ..... A01H 5/02
See application file for complete search history.

*Primary Examiner* — Kent L Bell
(74) *Attorney, Agent, or Firm* — C. A. Whealy

(57) ABSTRACT

A new and distinct cultivar of *Curcuma* plant named 'Curdossimp', characterized by its upright plant habit with outwardly arching leaves; moderately vigorous to vigorous growth habit; freely clumping growth habit; leaves with dark greyed orange-colored midveins; freely flowering habit; and large dense inflorescences with red purple-colored upper flower bracts positioned above the foliar plane on strung and erect peduncles.

3 Drawing Sheets

Botanical designation: *Curcuma alismatifolia.*
Cultivar denomination: 'CURDOSSIMP'.

BACKGROUND OF THE INVENTION

The present invention relates to a new and distinct cultivar of *Curcuma* plant, botanically known as *Curcuma alismatifolia* and hereinafter referred to by the name 'Curdossimp'.

The new *Curcuma* plant is a product of a controlled breeding program conducted by the Inventor in Naaldwijk, The Netherlands. The objective of the breeding program is to create new *Curcuma* plants that have uniform plant habit, good container performance and attractive inflorescence coloration.

The new *Curcuma* is a naturally-occurring whole plant mutation of *Curcuma alismatifolia* 'Curdossi', not patented. The new *Curcuma* plant was discovered and selected by the Inventor as a single flowering plant within a population of plants of 'Curdossi' in a controlled greenhouse environment in Naaldwijk, The Netherlands in May, 2016.

Asexual reproduction of the new *Curcuma* plant by axillary bud meristem culture in a controlled environment in Naaldwijk, The Netherlands since July, 2016 has shown that the unique features of this new *Curcuma* plant are stable and reproduced true to type in successive generations of asexual reproduction.

SUMMARY OF THE INVENTION

Plants of the new *Curcuma* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Curdossimp'. These characteristics in combination distinguish 'Curdossimp' as a new and distinct *Curcuma* plant:

1. Upright plant habit with outwardly arching leaves.
2. Moderately vigorous to vigorous growth habit.
3. Freely clumping growth habit.
4. Leaves with dark greyed orange-colored midveins.
5. Freely flowering habit.
6. Large dense inflorescences with red purple-colored upper flower bracts positioned above the foliar plane on strong and erect peduncles.

Plants of the new *Curcuma* differ from plants of the mutation plant, 'Curdossi', in the following characteristics:

1. Plants of the new *Curcuma* have more upper flower bracts as plants of 'Curdossi'.
2. Plants of the new *Curcuma* have red purple-colored upper flower bracts whereas plants of 'Curdossi' have medium purple-colorcd upper flower bracts.

Plants of the new *Curcuma* can also be compared to plants of *Curcuma alismatifolia* 'Curalimei', disclosed in U.S. Plant Pat. No. 25,124. In side-by-side comparisons plants of the new *Curcuma* differ from plants of 'Curalimei' in the following characteristics:

1. Plants of the new *Curcuma* are taller than plants of 'Curalimei'.
2. Plants of the new *Curcuma* are not as freely clumping as plants of 'Curalimei'.
3. Plants of the new *Curcuma* have broader leaves than plants of 'Curalimei'.
4. Plants of the new *Curcuma* have red purple-colored upper flower bracts whereas plants of 'Curalimei' have dark pink-colored flower bracts with dark red purple-colored apices.

BRIEF DESCRIPTION OF THE PHOTOGRAPHS

The accompanying photographs illustrate the overall appearance of the new *Curcuma* plant showing the colors as true as it is reasonably possible to obtain in colored reproductions of this type. Colors in the photographs may differ slightly from the color values cited in the detailed botanical description which accurately describe the colors of the new *Curcuma* plant.

The photograph on the first sheet is a side perspective view of a typical plant of 'Curdossimp' grown in a container.

The photograph on the second sheet is a close-up view of a leaf of 'Curdossimp'.

The photograph on the third sheet is a close-up view of a typical inflorescence of 'Curdossimp'.

DETAILED BOTANICAL DESCRIPTION

The aforementioned photographs and following observations and measurements describe plants grown during the winter in 17-cm containers in a glass-covered greenhouse in Naaldwijk, The Netherlands and under cultural practices typical of commercial *Curcuma* production. During the production of the plants, day temperatures ranged from 22° C. to 25° C., night temperatures ranged from 20° C. to 22° C. and light levels averaged 55 kilolux. Plants were 16 weeks old when the photographs and the detailed description were taken. In the following description, color references are made to The Royal Horticultural Society Colour Chart, 2015 Edition, except where general terms of ordinary dictionary significance are used.

Botanical classification: *Curcuma alismatifolia* 'Curdossimp'.

Parentage: Naturally-occurring whole plant mutation of *Curcuma alismatifolia* 'Curdossi', not patented.

Propagation:

*Type.*—By axillary bud meristem culture.

*Time to initiate roots.*—About ten days at temperatures about 23° C.

*Time to produce a rooted young plant.*—About 28 to 30 days at temperatures about 21° C.

*Root description.*—Medium in thickness, fibrous; typically white in color, actual color of the roots is dependent on substrate composition, water quality, fertilizer type and formulation, substrate temperature and physiological age of roots.

*Rooting habit.*—Moderately branching, medium density.

Plant description:

*Plant and growth habit.*—Upright plant habit with outwardly arching leaves; overall shape, obovate; freely clumping habit with about seven basal shoots forming per plant; moderately vigorous to vigorous growth habit and moderate growth rate.

*Plant height (soil level to top of foliar plane).*—About 62.5 cm.

*Plant height (soil level to top of inflorescences).*—About 79.8 cm.

*Plant diameter.*—About 77 cm.

Leaf description:

*Leaf arrangement.*—Alternate; simple.

*Length, fully expanded.*—About 77.5 cm.

*Width, fully expanded.*—About 9.5 cm.

*Shape.*—Narrowly oblanceolate.

*Apex.*—Apiculate.

*Base.*—Sheathing.

*Margin.*—Entire; unlobed.

*Venation.*—Parallel.

*Aspect.*—Initially upright, then outwardly arching.

*Texture and luster, upper and lower surfaces.*—Smooth, glabrous; non-rugose; matte.

*Color.*—Developing leaves, upper surface: Close to 143A. Developing leaves, lower surface: Close to between 138B and 146D. Fully expanded leaves, upper surface: Close to 137A to 137B; midvein, close to 166A; secondary venation, close to 143A. Fully expanded leaves, lower surface: Close to between 137C and 138A; venation, close to between 137C and 138A.

*Leaf sheaths.*—Length: About 20 cm. Width: About 1 cm. Texture and luster, upper surface: Smooth, glabrous; glossy. Texture and luster, lower surface: Smooth, glabrous; slightly glossy. Color, upper surface: Close to 144B; margins, close to 157D; venation, close to 144A. Color, lower surface: Close to 144A; margins, close to 157D; venation, close to 146A.

Inflorescence description:

*Arrangement.*—Dense and upright terminal spike inflorescences developing directly from the basal shoots with numerous showy upper flower bracts; typically each spike with about ten clusters each with about three flowers; about 60 flowers developing per plant at one time.

*Time to flower.*—In The Netherlands, plants flower from summer into autumn; flowering continuous during this period; plants begin flowering about ten weeks after planting.

*Flower longevity.*—Flowers last about three days on the plant; flowers persistent; plants maintain good substance for about 40 days.

*Fragrance.*—Faint; sweet and somewhat spicy.

*Flower buds.*—Length: About 2.6 cm. Diameter: About 7 mm. Shape: Elliptic. Texture and luster: Smooth, glabrous; glossy. Color: Proximally, close to 155A; mid-section, close to 158A to 158B; distally, close to N82A tinged with close to 83B.

*Inflorescence length.*—About 14.7 cm.

*Inflorescence diameter.*—About 8.6 cm.

*Flowers.*—Length: About 4.8 cm. Diameter: About 2 cm by 2.4 cm. Flower throat diameter: About 9 mm. Flower tube length: About 2.5 cm. Flower tube diameter: About 3.5 mm. Shape and arrangement: Zygomorphic with three petals, conspicuous labellum and two lateral corolla lobes (staminodia), fused towards the base; gamosepalous calyx with three sepals.

*Labellum.*—Length: About 4.8 cm. Width: About 1.9 cm. Shape: Narrowly spatulate; fused at the base. Apex: Praemorse. Margins: Entire; slightly to moderately undulate. Texture and luster, upper surface: Smooth, glabrous; slightly velvety; matte. Texture and luster, lower surface: Smooth, glabrous; slightly glossy. Color: When opening, upper surface: Close to 83A fading towards the base to close to 83D; central narrow stripe, close to 14A; proximal dots (two), close to 58C. When opening, lower surface: Close to 83A fading towards the base to close to 83C to 83D; central band, close to 155C. Fully opened, upper surface: Close to 83A to 83B fading towards the base to close to 83D; central narrow stripe, close to 14A; proximal dots (two), close to 58C; venation, close to 83A; color becoming closer to 71A to 71B with development. Fully opened, lower surface:

Close to 83A to 83B fading towards the base to close to 83D; central band, close to 155C; venation, close to N82B; color becoming closer to 71A to 71B with development.

*Lateral corolla lobes.*—Length: About 4.7 cm. Width: About 1.3 cm. Shape: Oblanceolate. Apex: Acute. Margins: Entire; slightly to moderately undulate. Texture and luster, upper surface: Smooth, glabrous; matte. Texture and luster, lower surface: Smooth, glabrous; slightly glossy. Color: When opening, upper and lower surfaces: Close to. N82C fading towards the base to close to 85D. Fully opened, upper and lower surfaces: Close to N82C fading towards the base to close to 85D; venation, close to N82B to N82C; color becoming closer to 71A to 71B with development.

*Petals.*—Length, dorsal petal: About 4 cm. Length, lateral petals: About 4.2 cm. Width, dorsal petal: About 1.1 cm. Width, lateral petals: About 7 mm. Shape, dorsal petal: Oblanceolate. Shape, lateral petals: Narrowly oblanceolate. Apex, dorsal petal: Broadly acute. Apex, lateral petals: Acute. Margins, all petals: Entire; not undulate. Texture and luster, upper surface: Smooth, glabrous; matte. Texture and luster, lower surface: Smooth, glabrous; slightly glossy. Color, dorsal and lateral petals: When opening, upper surface: Close to N82D fading towards the base to close to NN155D. When opening, lower surface: Close to N82C fading towards the base to close to NN155D. Fully opened, upper surface: Close to N82D fading towards the base to close to NN155D; venation, similar to lamina colors; color does not change with development. Fully opened, lower surface: Close to N82C to N82D fading towards the base to close to NN155D; venation, similar to lamina colors; color does not change with development. Color, flower throat: Close to NN155A; venation, close to NN155A. Color, flower tube: Close to NN155A; venation, close to NN155A.

*Calyx.*—Length: About 1.1 cm. Diameter: About 6 mm. Quantity of sepals and arrangement: Three in a single whorl; fused at the base. Sepal length: About 1.1 cm. Sepal width: About 4 mm. Sepal shape: Narrowly obovate. Sepal apex: Acute. Sepal base: Broadly cuneate. Sepal margin: Entire. Sepal texture and luster, upper and lower surfaces: Smooth, glabrous; moderately glossy. Sepal color: When opening and fully opened, upper surface: Close to NN155D; distally, close to N80D. When opening and fully opened, lower surface: Close to NN155D; distally, close to N80D.

*Upper flower bracts.*—Quantity: About nine upper bracts per inflorescence. Length: About 7.8 cm. Width: About 5.2 cm. Shape: Ovate, slightly carinate. Apex: Broadly acute. Base: Cuneate. Margin: Entire; not undulate. Texture and luster, upper and lower surfaces: Smooth, glabrous; moderately glossy. Color: When opening and fully opened, upper surface: Close to 72B to 72C; distally, close to 197A to 197B; venation, similar to lamina and distally, close to 197A to 197B. When opening and fully opened, lower surface:. Close to 72B to 72C; distally, close to between 197A and N199A; venation, similar to lamina and distally, close to between 197A and N199A.

*Lower flower bracts.*—Quantity: About nine lower bracts per inflorescence. Length: About 4.1 cm. Width: About 3.8 cm. Shape: Broadly obovate to inverted reniform, strongly concave. Apex: Obtuse. Base: Cuneate. Margin: Entire; undulate. Texture and luster, upper and lower surfaces: Smooth, glabrous; moderately glossy. Color: When opening and fully opened, upper surface: Close to between 146D to 147D fading distally to close to 146A with blotch, close to 59C; venation, similar to lamina. When opening and fully opened, lower surface: Close to 144B fading distally to close to 144A with blotch, close to 183A; venation, similar to lamina.

*Peduncles.*—Length: About 61.4 cm. Diameter: About 8 mm. Strength: Strong. Aspect: Erect to about 5° from vertical. Texture and luster: Smooth, glabrous; slightly glossy. Color: Close to 144A fading proximally to close to 144B.

*Stamens.*—Quantity: Two per flower; fused. Filament length: About 1.6 cm. Filament diameter: About 5 mm. Filament color: Close to NN155C; distally tinged with close to 83C. Anther length: About 8 mm. Anther width: About 1 mm. Anther shape: Narrowly oblong. Anther color: Close to 155A. Pollen amount: Moderate. Pollen color: Close to 155C.

*Pistils.*—Quantity per flower: One. Pistil length: About 4 cm. Style length: About 3.8 cm. Style color: Close to NN155D. Stigma diameter: About 2 mm. Stigma shape: Cupped. Stigma color: Close to NN155D. Ovary color: Close to 150D.

*Seeds and fruits.*—To date, seed and fruit development have not been observed on plants of the new *Curcuma.*

Pathogen & pest resistance: To date, plants of the new *Curcuma* have not been observed to be resistant to pathogens or pests common to *Curcuma* plants.

Temperature tolerance: Plants of the new *Curcuma* have been observed to be tolerant to temperatures ranging from about 5° C. to about 40° C. and are suitable for USDA Hardiness Zones 10 to 12.

It is claimed:

1. A new and distinct *Curcuma* plant named 'Curdossimp' as illustrated and described.

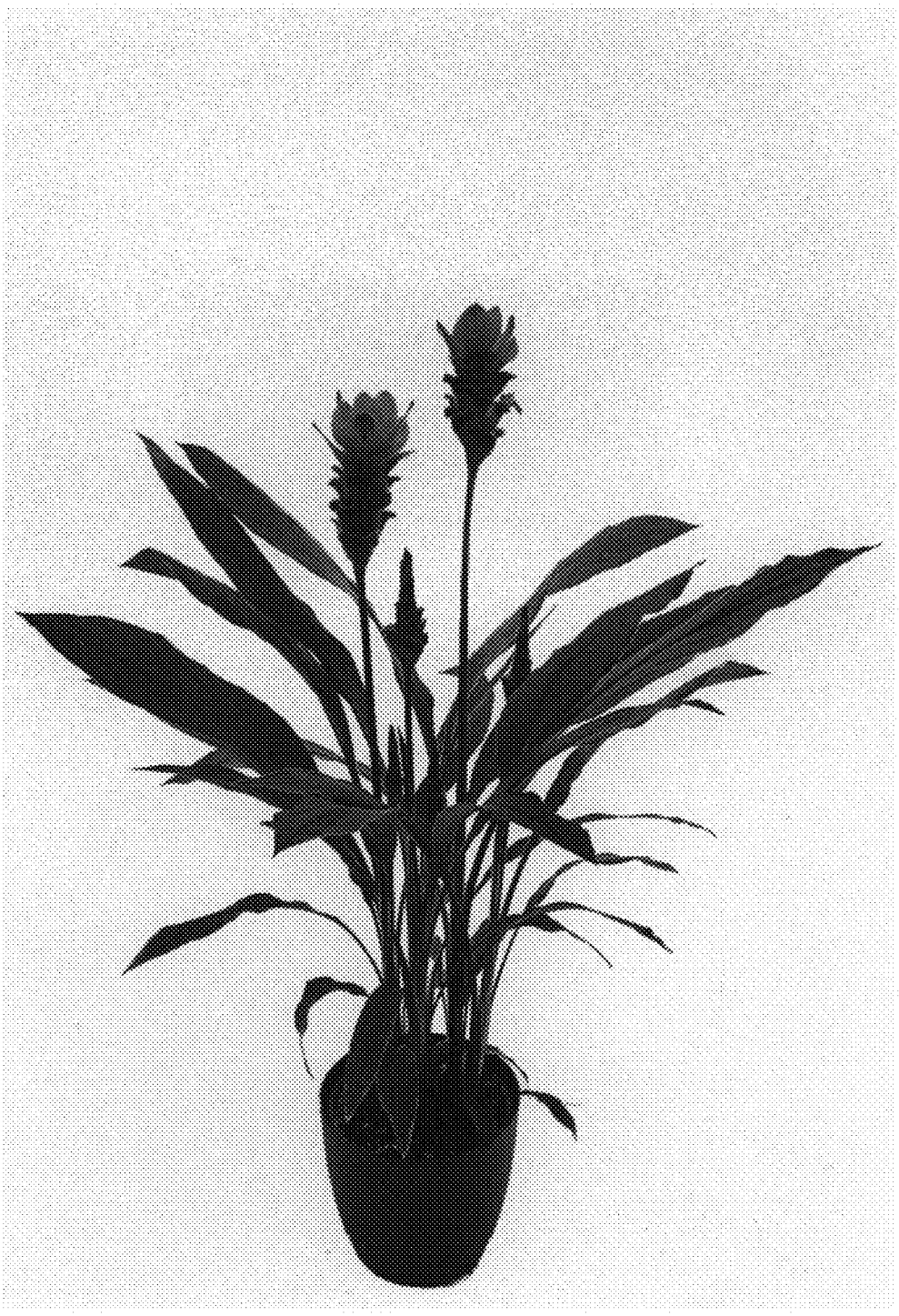

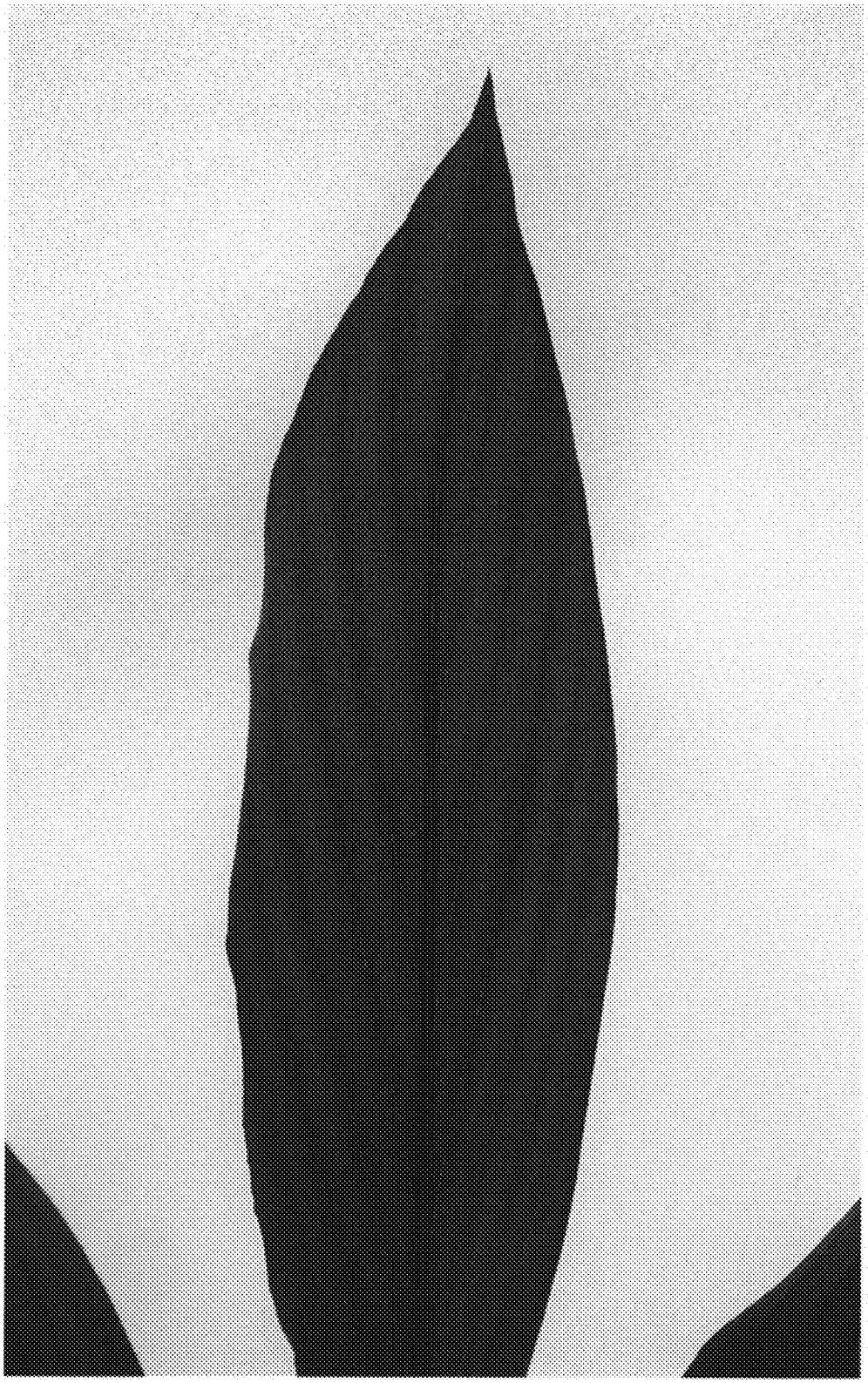

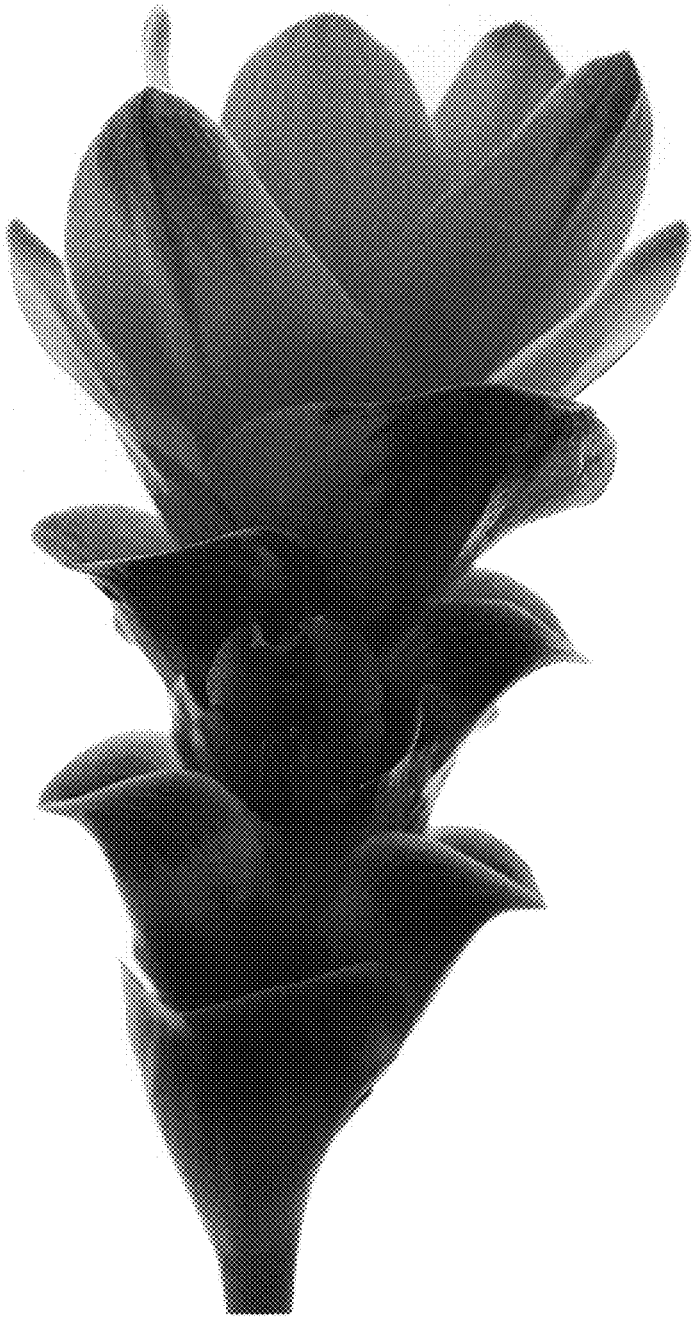

* * * * *